(12) United States Patent
Mentelos

(10) Patent No.: US 7,818,058 B2
(45) Date of Patent: Oct. 19, 2010

(54) AUTOMATED ECG LEAD IMPEDANCE MEASUREMENT INTEGRATED INTO ECG GATING CIRCUITRY

(75) Inventor: Richard A. Mentelos, Guilford, CT (US)

(73) Assignee: Ivy Biomedical Systems, Inc., Branford, CT (US)

( * ) Notice: Subject to any disclaimer, the term of this patent is extended or adjusted under 35 U.S.C. 154(b) by 1090 days.

(21) Appl. No.: 11/509,928

(22) Filed: Aug. 25, 2006

(65) Prior Publication Data

US 2008/0051845 A1   Feb. 28, 2008

(51) Int. Cl.
*A61N 1/00* (2006.01)
(52) U.S. Cl. ......................................... 607/8
(58) Field of Classification Search ...................... 607/8; 600/41, 481, 301; 128/899
See application file for complete search history.

(56) References Cited

U.S. PATENT DOCUMENTS

| 4,245,643 | A | | 1/1981 | Benzing, III et al. |
| 5,337,230 | A | | 8/1994 | Baumgartner et al. |
| 5,904,654 | A | * | 5/1999 | Wohltmann et al. ......... 600/481 |
| 6,347,245 | B1 | | 2/2002 | Lee et al. |
| 6,463,326 | B1 | | 10/2002 | Hartley et al. |
| 6,887,239 | B2 | * | 5/2005 | Elstrom et al. ................ 606/41 |
| 2004/0172080 | A1 | | 9/2004 | Stadler et al. |
| 2005/0183733 | A1 | * | 8/2005 | Kawano et al. ............. 128/899 |
| 2010/0063365 | A1 | * | 3/2010 | Pisani et al. ................ 600/301 |

FOREIGN PATENT DOCUMENTS

| EP | 0182197 A2 | 5/1986 |
| JP | 02-243988 A | 9/1990 |

OTHER PUBLICATIONS

International Search Report of the International Searching Authority for PCT/US2007/018391, mailed from the International Searching Authority on Jan. 21, 2008.
Written Opinion of the International Searching Authority for PCT/US2007/018391, mailed from the International Searching Authority on Jan. 21, 2008.

* cited by examiner

*Primary Examiner*—George Manuel
(74) *Attorney, Agent, or Firm*—K&L Gates LLP

(57) ABSTRACT

The present invention relates to a system and method for determining the impedance of an electrode at the electrode-body interface. The electrode-body impedance of one of the electrodes may be calculated using the voltage difference between that electrode and a plurality of other electrodes, and the voltage and impedance of an alternating current generator in communication with the electrodes.

20 Claims, 3 Drawing Sheets

AUTOMATED ECG LEAD IMPEDANCE MEASUREMENT INTEGRATED INTO ECG GATING CIRCUITRY

FIELD OF THE INVENTION

The present invention relates to ECG monitoring and gating systems, and specifically to improved systems and methods for measuring the impedance at the electrode-body interface.

BACKGROUND OF THE INVENTION

Everyday, in hospitals around the world, the electrical activity of humans and animals is measured by countless doctors and veterinarians through the use of electrodes. In some instances, an ECG of the heart is taken to monitor or measure heart abnormalities. Other patients have brainwaves monitored or measured through an EEG. Still other patients require stress tests. Additionally, defibrillators apply electricity to patients through electrodes to stimulate the patient's heart. Through all these procedures and tests, the interface between the patient and the electrode, the electrode-body interface, controls the quality of the signal transferred through the interface. High impedance, i.e. high resistance to the flow of electricity at the electrode-body interface may result in poor signal transmission.

The quality of the electrical signal transferred through the electrode-body interface affects each one of the above mentioned procedures. For an ECG measurement, whether the measurement is simply to monitor the patient's heart cycle or to trigger or gate a device, such as a gamma camera, to record an image of the heart, noise in the signal can negatively affect the results. Noise in the signal can cause improper triggering of the gamma camera and require multiple tests. Additionally, poor electrical signal transfer through the electrode-body interface can cause burning of the skin during defibrillation.

Currently, medical staff attempt to reduce the impedance at the electrode-body interface by eliminating all interfering substances from the skin surface. Medical staff, including nurses and technicians, scrub and cleanse the skin's surface to remove excess debris, oil, hair and any other particles that could raise the impedance at the electrode-body interface. However, without measuring the impedance at the electrode-body interface, the medical staff have no concrete indicator of the impedance of the interface.

Most medical staff use hand-held impedance measurement devices that can measure the impedance at the electrode-body interface. However, these devices are clumsy and time consuming. Each electrode has to be measured individually and each medical staff member has to carry an electrode impedance measuring device.

An early warning system is needed to alert medical technicians that the patient preparation is not finished, and that preparation needs to be continued until an acceptable electrode-body impedance is reached. Therefore, a need exists to automate and facilitate the process of measuring the impedance at the electrode-body interface and provide an early warning system of improper electrical impedance.

SUMMARY OF THE INVENTION

In satisfaction of these needs and others, the present invention relates to automating the measurement of impedance at the electrode-body interface.

In one aspect, the present invention relates to a system for measuring the impedance at the electrode-body interface. The system includes a processor, an alternating current generator in communication with the processor, and a plurality of electrodes in communication with the processor and the alternating current generator. The processor calculates the impedance at the electrode-body interface using the output impedance and output voltage of the alternating current generator and the voltage between one or more of the electrodes.

In some embodiments, the alternating current generator provides a constant current output. In these embodiments, the impedance at the electrode-body interface is linearly related to the voltage between one or more of the electrodes.

In some embodiments, the system further includes a plurality of switches, each of which is associated with a respective electrode. In some of these embodiments, the switches are field effect transistors.

In some embodiments, the system further includes a synchronous rectifier in electrical communication between the processor and the electrodes. In some of these embodiments, the synchronous rectifier is also in communication with the alternating current generator. The synchronous rectifier samples the peak amplitude of a waveform generated by the alternating current generator.

In some embodiments, the plurality of electrodes includes three electrodes. The voltage between the electrodes is then calculated by paralleling two of the electrodes while measuring the voltage between the parallel electrode and the third electrode.

In some embodiments, the alternating current generator operates at 10 hertz and generates a triangular voltage waveform. The alternating current generator in some embodiments generates currents of less than 10 microamps.

In some embodiments, the system further includes an analog to digital converter in electrical communication between the processor and the synchronous rectifier.

Another aspect of the present invention relates to incorporating the system for measuring the ECG impedance at the electrode-body interface into other systems or clinical devices such as a gamma camera system, a stress testing system, a defibrillator system, an EEG system, a transcutaneous nerve stimulator, a depth of anesthesia monitoring system, an EMG monitor, a CT scanner, a MRI, an ultrasound, a lithotripter, and any other device for which skin electrodes are required for measurement or current delivery. The user of each of the enumerated systems is automatically notified of the electrode-body impedance.

Yet another aspect of the present invention relates to a method for measuring the impedance at the body-electrode interface in a system that includes an alternating current generator and a plurality of electrodes. The method includes measuring an output impedance and an output voltage of the alternating current generator, measuring a voltage between two or more of a plurality of electrodes in communication with the alternating current generator and calculating the impedance at the electrode-body interface using the output impedance and output voltage of the alternating current generator and the voltage between two or more electrodes.

In some embodiments, the alternating current generator provides a constant current output. In these embodiments, the impedance at the electrode-body interface is linearly related to the voltage between one or more of the electrodes.

In some embodiments, the plurality of electrodes comprises three electrodes. The voltage between two or more electrodes is then calculated by paralleling two of the electrodes while measuring the voltage between the parallel electrode and the third electrode.

In some embodiments, the alternating current generator operates at 10 hertz and generates a triangular voltage waveform. The alternating current generator in one embodiment generates currents of less than 10 microamps.

BRIEF DESCRIPTION OF THE DRAWINGS

These embodiments and other aspects of this invention will be readily apparent from the description below and the appended drawings, which are meant to illustrate and not to limit the invention, and in which.

DESCRIPTION

The present invention will be more completely understood through the following description, which should be read in conjunction with the attached drawings. In this description, like numbers refer to similar elements within various embodiments of the present invention. Within this description, the claimed invention will be explained with respect to embodiments. However, the skilled artisan will readily appreciate that the methods and systems described herein are merely exemplary and that variations can be made without departing from the spirit and scope of the invention.

In general, the present invention relates to a system and method for determining the impedance of an electrode, for example a skin electrode, at the electrode-body interface. The electrode may be used in ECG and EEG gating and monitoring, defibrillators, stress testing, transcutaneous nerve stimulators, depth of anesthesia monitoring systems, EMG monitors, CT scanners, MRIs, ultrasounds, lithotripters, and any other device for which skin electrodes are required for measurement or current delivery. The electrode-body impedance of one of the electrodes may be calculated using the voltage difference between that electrode and a plurality of other electrodes, and the voltage and impedance of an alternating current generator in communication with the electrodes.

Figure 1:
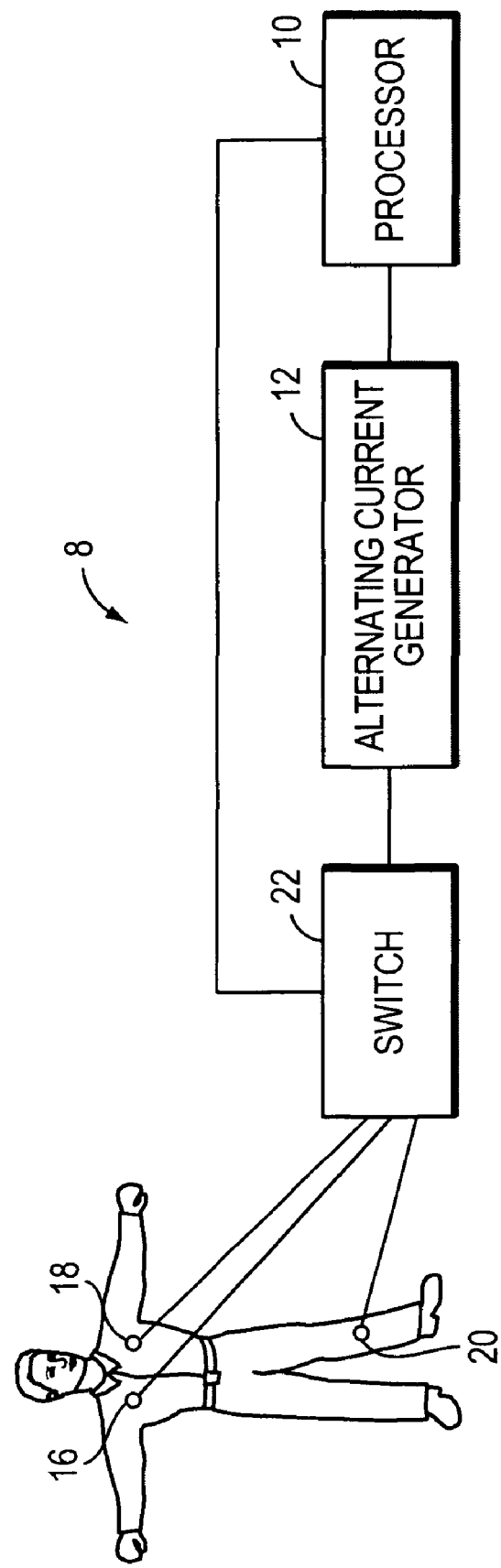
FIG. 1 is a schematic diagram illustrating an automated electrode-body interface impedance measurement circuit according to an embodiment of the present invention.

FIG. 1 is a highly schematic diagram illustrating an automated electrode-body interface impedance measurement system, according to an embodiment of the present invention. In one embodiment, the impedance measurement system 8 includes a processor 10, an alternating current generator 12, a switch 22, and a plurality of electrodes. In one embodiment, there is a first electrode 16, a second electrode 18, and a third electrode 20.

In one embodiment, a plurality of electrodes, for example three electrodes 16-20, are connected to the switch 22. The switch 22 is in electrical communication with both the alternating current generator 12 and the processor 10 and permits the user to select the appropriate electrodes 16-20 for the selected impedance measurement, for example, the first electrode 16. The processor 10 controls both the alternating current generator 12 and the switch 22. The processor 10 turns on the alternating current generator 12, to enable the impedance measurement, and turns off the alternating current generator 12 after the calculation has been completed. The alternating current generator 12 applies a voltage through the switch 22, which causes a current to flow to the first electrode 16, through the patient, to the second electrode 18 and the third electrode 20, which may be paralleled. The processor 10 measures the resultant voltage and uses that voltage along with the impedance of and voltage of the alternating current generator 12 to calculate the impedance of the electrodes 16-20. The measurement and calculation is then repeated for each of the two remaining electrodes 18 and 20.

With continued reference to FIG. 1, the electrodes may be any electrode used by one of skill in the art to measure electrical activity in a patient. Depending on what electrical activity is being measured, there can be three, four, five, six, or more electrodes. For ECG monitoring and gating, three or more electrodes may be used. For EEG monitoring and gating as few as two and as many as 64 electrodes may be used. For a stress test, up to twelve electrodes may be used. For a defibrillator, two or more electrodes may be used. In the illustrated embodiment, three electrodes are shown to measure the ECG of a patient. Although other types of measurements are possible and more electrodes may be used, in discussing the aspects of the present invention, an exemplary three electrodes will be used in connection with an ECG monitor.

With continued reference to FIG. 1, the alternating current generator 12 may be a 10 hertz generator that produces an alternating current which is applied to the electrodes 16-20. The alternating current generator 12 may produce a current in the range or 10-15 microamps RMS. The alternating current generator 12 may produce a variety of waveforms, including triangular or square voltage waveforms. The alternating current generator 12 has an output voltage associated with it, in the range of 0.5 volts RMS to 5.0 volts RMS and an output impedance in the range 350 kohms to 450 kohms.

The voltage between the electrodes 16-20 is one parameter that is used to determine a selected electrode's impedance. Since it is difficult to have a zero ohm reference point on a patient's body, the measurement of the impedance of one electrode, for example, the first electrode 16, in one embodiment is made by paralleling, i.e. electrically shorting together, the other two electrodes, i.e. the second electrode 18 and the third electrode 20. Then, the voltage difference between the first electrode 16 and the parallel combination of the second electrode 18 and the third electrode 20 is used for the calculation of the impedance at the electrode-body interface of the first electrode 16.

In one embodiment, the current generator 12 produces a constant current output. With a constant current output, the impedance of an electrode is linearly related to the voltage between the electrodes, i.e. the impedance of the first electrode 16 is linearly related to the voltage difference between the first electrode 16 and the voltage of the parallel combination of the second electrode 18 and the third electrode 20, as governed by the following equation:

$$Z_2 = kE_2 \qquad \text{Eqn. 1}$$

where $Z_2$ is the unknown impedance, k is an empirical constant of proportionality and $E_2$ is the voltage difference between the first electrode 16 and the parallel combination of the second electrode 18 and the third electrode 20.

However, it may be difficult and expensive to use a constant current source. Therefore, in another embodiment, the alternating current generator 12 produces a variable current. When the alternating current generator 12 produces a variable current, the relationship between the voltage difference between the first electrode 16 and the voltage of the parallel combination of the second electrode 18 and the third electrode 20, and the impedance of the first electrode 16 is no longer linear. Rather it is governed by the following equation:

$$Z_2 = \frac{Z_1}{\frac{E_1}{E_2} - 1} \qquad \text{Eqn. 2}$$

where $Z_2$ is the unknown impedance of the first electrode 16, $Z_1$, is the impedance of the alternating current generator 12, $E_1$ is the output voltage of the alternating current generator 12, and $E_2$ is the voltage difference between the first electrode 16 and the parallel combination of the second electrode 18 and the third electrode 20. The output voltage and the impedance of the alternating current generator 12 are set values that are set by either the medical staff or set upon manufacture of the impedance measurement system 8.

With continued reference to FIG. 1, the processor 10, in various embodiments, is a microprocessor, a desktop or laptop computer, an embedded chip, or any type of processor that can be pre-programmed to perform calculations based on the measured voltages and impedance. The processor 10 controls the alternating current generator 12 and performs the impedance calculations. As discussed above, the type of calculation that the processor 10 performs is based on the whether the current output of the alternating current generator 12 is variable or constant. If the output current is constant, the processor 10 will perform the calculation in Eqn. 1 to determine the unknown impedance. If the output current is variable, the processor 10 will perform the calculation in Eqn. 2 to determine the unknown impedance.

In some embodiments, the processor may also control a signal to trigger or gate another device, such as an ECG monitor or a gamma camera.

Figure 2:
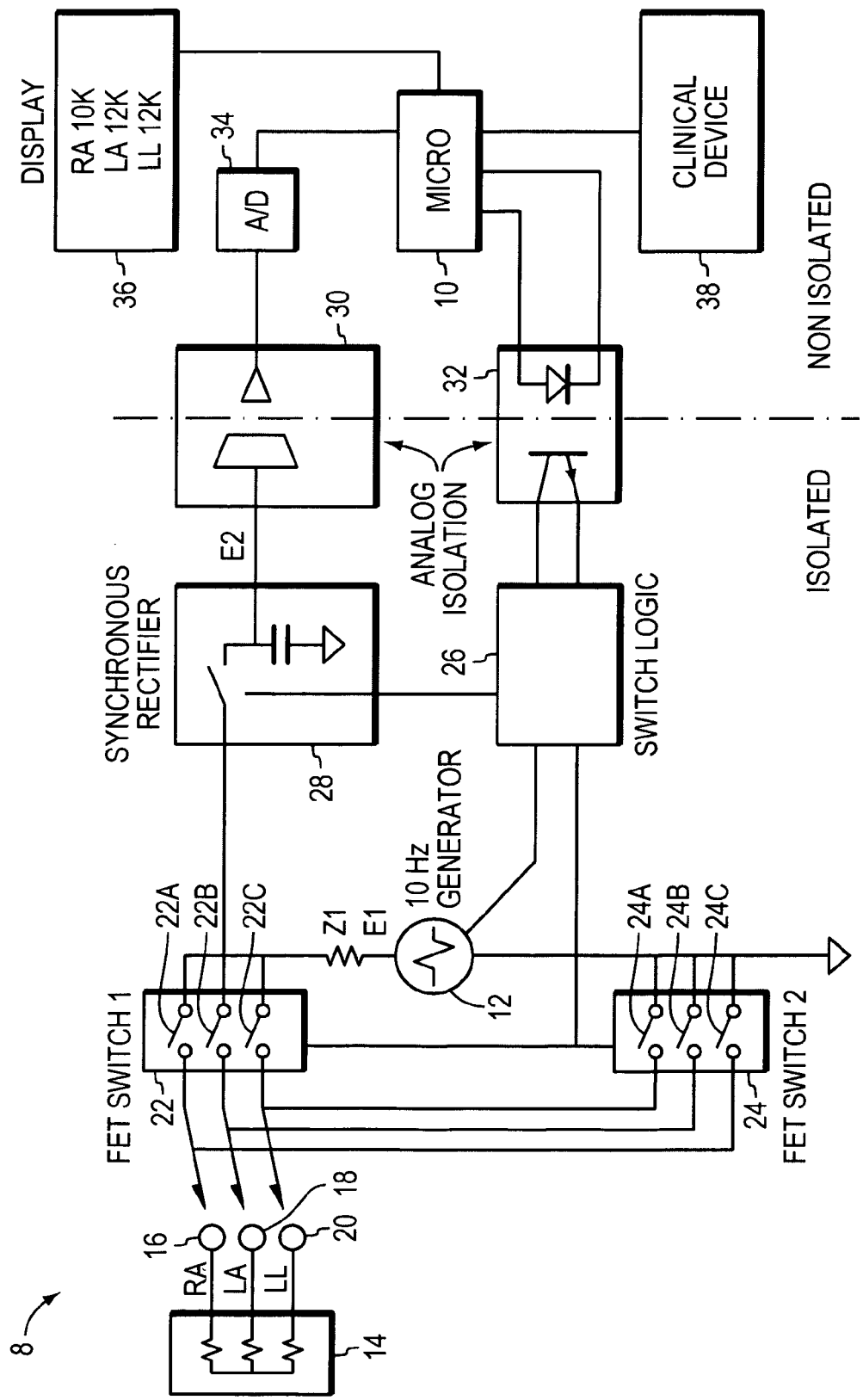
FIG. 2 is a schematic diagram illustrating an automated electrode-body interface impedance measurement circuit according to an embodiment of the present invention.

FIG. 2 is a more detailed schematic diagram of the system of FIG. 1, illustrating an automated electrode-body interface impedance measurement system according to an embodiment of the present invention. In this embodiment, the impedance measurement system 8 includes a processor 10; an alternating current generator 12; a plurality of electrodes (a first electrode 16, a second electrode 18, and a third electrode 20); two sets of switches (a first switch set 22 and a second switch set 24); a switch logic device 26; a synchronous rectifier 28; a plurality of isolators (a first isolator 30 and a second isolator 32); an analog to digital converter 34; a display 36; and optionally a clinical device 38.

In one embodiment, a plurality of electrodes, preferably three, are connected to a first switch set 22 and a second switch set 24. Each switch set 22 and 24 contain one or more internal switches. An exemplary switch set 22, 24 contains three internal switches, one for each electrode: a first internal switch 22A, a second internal switch 22B, a third internal switch 22C, a fourth internal switch 24A, a fifth internal switch 24B, and a sixth internal switch 24C. Each of the switch sets 22 and 24 are connected to the alternating current generator 12. The alternating current generator 12 applies a voltage and a current flow to the three electrodes 16-20. In this embodiment, the switch sets 22 and 24 and the alternating current generator 12 are controlled by the switch logic device 26, which is in turn controlled by the processor 10. The processor 10 turns on the switch logic device 26, the synchronous rectifier 28, the analog to digital converter 34, and the alternating current generator 12 (to apply a voltage to the electrodes 16-20), and sets the switch sets 22 and 24 and the internal switches 22A-C and 24A-C.

Once the impedance measurement system 8 is turned on, the impedance of each of the electrodes is measured. For example, a signal, corresponding to the voltage difference between the first electrode 16 and the paralleled second electrode 18 and third electrode 20, is rectified by the synchronous rectifier 28 and converted to a digital signal by the analog to digital converter 34, after passing through the isolator 30. The voltage difference is then read by the processor 10. The processor 10, using the above equations, will use this voltage value alone where the generator 12 is a constant current generator or in combination with the voltage and impedance of the alternating current generator 12, if the generator 12 is variable, to calculate the impedance of the first electrode 16. Once the processor 10 has performed the calculation, the display 36 will register a value for the electrode-body impedance of the first electrode 16. The process is then repeated first for the second electrode 18 and then for the third electrode 20. The process of calculating all three electrode-body impedance values may take approximately 0.4 to 1.0 seconds, but preferably 0.6 seconds. Additionally, a clinical device 36 may also be controlled by the processor 10 and connected to the impedance measurement system 8. Once the calculation of the electrode-body impedance of all three electrodes is completed, the processor shuts off the synchronous rectifier 26, the alternating current generator 12, and the analog to digital to converter 34.

With continued reference to FIG. 2, the plurality of switches are not limited to two switch sets 22, 24, but can include any number of switch sets 22, 24 necessary for the number of electrodes being used. The switch sets 22, 24 may be used to isolate the appropriate electrode. For example, if the impedance of the first electrode 16 is to be measured, the switch sets 22, 24 will be set to create a circuit between the first electrode 16 and the paralleled second electrode 18 and the third electrode 20. More specifically, the first internal switch 24A (corresponding to the first electrode 16) will be closed and the second and third internal switches 22B and 22C (corresponding to the second electrode 18 and the third electrode 20, respectively) will remain open in the first switch set 22. In the second switch set, the fifth and sixth internal switches 24B and 24C (corresponding to the second electrode 18 and the third electrode 20) will be closed, while the fourth internal switch 24A (corresponding to the first electrode 16) will remain open. In one embodiment, the first switch set 22 and the second switch set 24 comprise field effect transistor ("FET") switches.

The switch logic device 26 controls the switches 22 and 24, through the processor 10. In one embodiment, the processor 10 produces a digital output to the switch logic device 26. For example, upon receipt of the first digital output from the processor 10, the switch logic device 26 turns on the alternating current generator 12. The switch logic device 26 then directs the first switch set 22 to close the first internal switch 22A and open the second and third internal switches 22B, 22C. A third digital output causes the second switch 24 to open fourth internal switch 24A and close the fifth and sixth internal switches 24B, 24C. Upon receipt of the fourth pulse, the switch logic device 26 turns off the alternating current generator 12. The sequence may be repeated to determine the impedance of the second electrode 18 and the third electrode 20. The alternating current generator 12 is shut off as the alternating current generator 12 may cause interference with the ECG signal when the impedance measurement system 8 is used with, for example, an ECG monitoring or gating device.

The synchronous rectifier 28 rectifies the signal from the alternating current generator 12. A full wave rectifier may be used, but the use of a synchronous rectifier expedites the sampling of the peak amplitude of the waveform generated by the alternating current generator 12.

The plurality of isolators (the first isolator 30 and the second isolator 32) are used to isolate the patient or body 10 from the high voltage electronics. The first isolator 30 and the second isolator 32 may be optical isolators, transformers, or analog isolators.

The analog to digital converter 34 converts the analog signal from the synchronous rectifier 28 into a digital signal to be read by the processor 10. As illustrated, the analog to digital converter 34 is on the non-isolated side of the impedance measurement system 8. However, in other embodiments, the analog to digital converter may be located on the isolated side of the impedance measurement system 8.

The display 36 may be any device known to one of skill in the art to display the output of a processor, such as a computer monitor or a LCD screen. The display 36 may show the electrode-body impedance for all of the electrodes used in the monitoring or triggering process to be performed. Three electrodes are illustrated in FIG. 2, thus, the display 36 will show the impedance of the first electrode 16, the second electrode 18, and the third electrode 18.

Other embodiments of the display 36 may include a series of blinking lights to indicate the impedance level at the electrode-body interface. For example a pair of red and green lights may be used: red signaling that the impedance is too high, green signaling an acceptable impedance. Additionally, three lights, red, green and yellow may be used, where yellow serves as a warning that the impedance may not be at an optimal level. A user, such as the medical staff, or the service provider for the system, may pre-configure the impedance levels for each of the blinking lights. Alternatively, an alarm may sound when the impedance level of the electrode-body interface for an electrode is too high. The alarm signals to the medical staff to continue to prepare the patient.

Another aspect of the invention relates to implementing the impedance measurement system 8 within the clinical device 38. The clinical device 38 may be, but is not limited to, the following: a gamma camera, a stress test ECG, an EEG machine, an EEG monitor, a transcutaneous nerve stimulator, a depth of anesthesia monitoring system, an EMG monitor, a CT scanner, a MRI, an ultrasound, a lithotripter, a defibrillator, or any other device for which skin electrodes are required for measurement or current delivery. The impedance measurement system 8 functions as described above. Once the impedance is measured, the medical staff may proceed to implement the clinical device 38. In one embodiment, the impedance measurement system 8 simply alerts the user of the other device of the impedance level at the electrode-body interface. Once the medical staff is alerted, the medical staff may proceed with the operation of the clinical device 38 or the medical staff may continue the preparation of the patient. In one embodiment, the impedance measurement system 8 will shut off the clinical device, such that the clinical device 38 will not operate until the impedance at the electrode-body interface has reached a pre-set level.

Figure 3:
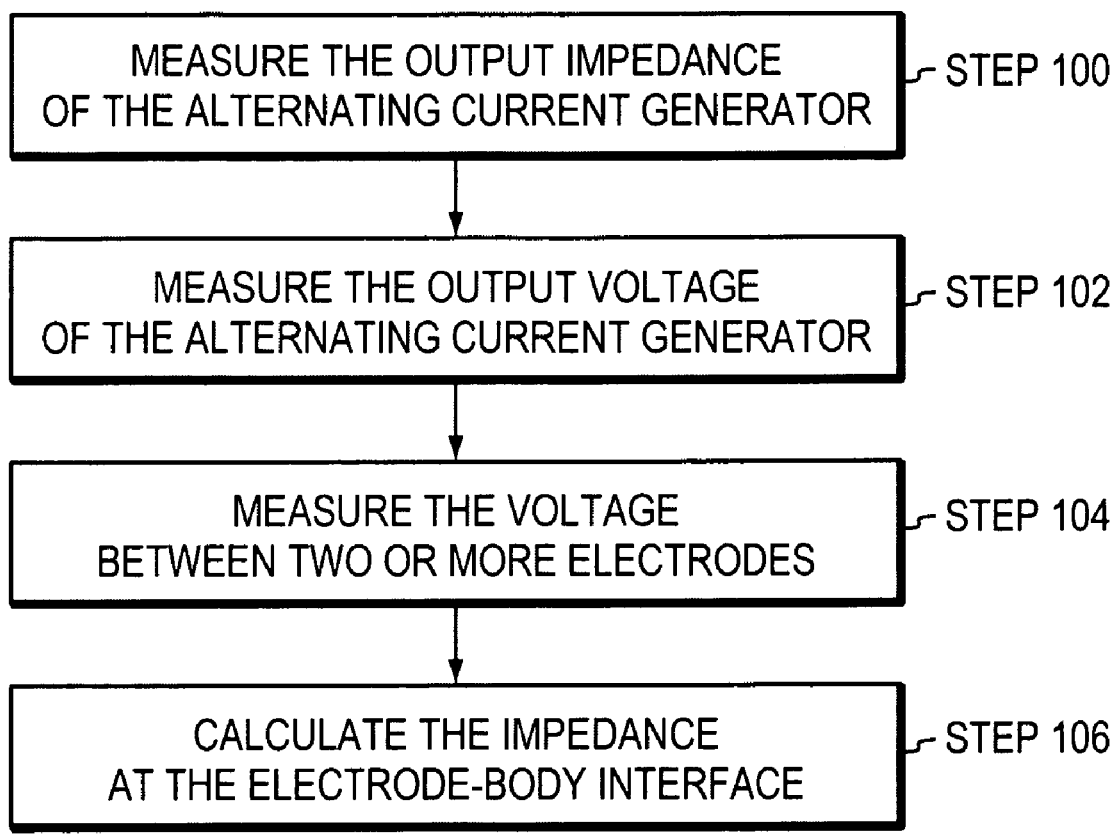
FIG. 3 is a high-level flow chart illustrating exemplary steps involved in calculating electrode-body interface impedance according to an embodiment of the present invention.

FIG. 3 is a high-level flow chart illustrating exemplary steps involved in calculating electrode-body interface impedance according to an embodiment of the present invention. The steps include (1) measuring an output impedance of the alternating current generator (Step 100); (2) measuring an output voltage of the alternating current generator (Step 102); (3) measuring a voltage between two or more electrodes (Step 104); and (4) calculating an impedance at the electrode-body interface (Step 106). The calculation of the impedance at the electrode-body interface is performed using either Eqn. 1 or Eqn. 2 above, depending of whether the alternating current produces a constant current or a variable current, respectively.

Variations, modification, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A system for measuring an impedance at the electrode-body interface comprising:
   a processor;
   an alternating current generator in communication with the processor, the alternating current generator having an output voltage and an output impedance; and
   a plurality of skin electrodes in communication with the processor and the alternating current generator, each skin electrode having an electrode impedance; and
   a display in communication with the processor configured to indicate the electrode impedance at the electrode-body interface for each skin electrode and generate an alert when one of the electrode impedances exceeds a preset level, wherein the processor calculates each electrode impedance at the electrode-body interface in response to the output impedance of the alternating current generator, the output voltage of the alternating current generator and the voltage between two or more of the skin electrodes, the alert indicating that an acceptable electrode impedance has not been reached.

2. The system of claim 1 wherein the alternating current generator provides a constant current output.

3. The system of claim 2 wherein each electrode impedance at the electrode-body interface is linearly related to the voltage between two or more of the skin electrodes.

4. The system of claim 1 further comprising a plurality of switches, each switch associated with a respective skin electrode.

5. The system of claim 4 wherein the switches are field effect transistors.

6. The system of claim 1 further comprising a synchronous rectifier in electrical communication between the processor and the skin electrodes.

7. The system of claim 6 wherein the synchronous rectifier is further in communication with the alternating current generator and samples a peak amplitude of a waveform generated by the alternating current generator.

8. The system of claim 1 wherein the plurality of skin electrodes comprise three electrodes.

9. The system of claim 8 wherein the voltage between two or more of the skin electrodes is measured by paralleling two of the skin electrodes while measuring the voltage of the third skin electrode.

10. The system of claim 1 wherein the alternating current generator operates at a frequency of 10 Hz.

11. The system of claim 1 wherein the alternating current generator generates a current of less than 50 microamps RMS.

12. The system of claim 1 wherein the alternating current generator generates a current of 10 microamps RMS.

13. The system of claim 1 wherein the alternating current generator generates a triangular voltage waveform.

14. The system of claim 1 further comprising an analog to digital converter in electrical communication between the processor and the synchronous rectifier.

15. The system of claim 1 further comprising an analog to digital converter in electrical communication between the processor and the skin electrodes.

16. A clinical system comprising:
a plurality of skin electrodes for attachment to a body of a patient and each of said skin electrodes having an electrode impedance;
a clinical device in communication with the skin electrodes; and
an impedance measuring device in electrical communication with the clinical device, the impedance measuring device comprising:
a processor in communication with the skin electrodes;
an alternating current generator in communication with the processor and the plurality of skin electrodes, the alternating current generator having an output voltage and an output impedance; and
a display in communication with the processor configured to indicate the electrode impedance at the electrode-body interface for each skin electrode and generate an alert when one of the electrode impedances exceeds a preset level, wherein the processor calculates the electrode impedance at the electrode-body interface in response to the output impedance of the alternating current generator, the output voltage of the alternating current generator and the voltage between two or more of the electrodes.

17. The system of claim 16 wherein the clinical device is a device for which skin electrodes are required for one of measurement or current delivery.

18. The system of claim 17 wherein the clinical device is selected from the group consisting of a transcutaneous nerve stimulator, a depth of anesthesia monitoring system, an EMG monitor, a CT scanner, a MRI, an ultrasound, or a lithotripter.

19. The clinical system of claim 16 wherein the clinical device is selected from the group consisting of: a gamma camera, an ECG device, a defibrillator, an EEG device, a stress testing system, a transcutaneous nerve stimulator, a depth of anesthesia monitoring system, an EMG monitor, a CT scanner, a MRI, an ultrasound and a lithotripter.

20. A method for measuring an impedance at an body-electrode interface in a system comprising an alternating current generator and a plurality of skin electrodes, the method comprising:
measuring an output impedance of the alternating current generator;
measuring an output voltage of the alternating current generator;
measuring a voltage between two or more skin electrodes of the plurality of skin electrodes in communication with the alternating current generator;
calculating an impedance for each of the plurality of skin electrodes at the electrode-body interface using the output impedance of an alternating current generator, the output voltage of the alternating current generator and the voltage between two or more skin electrodes; and
generating an alert when the calculated impedance for one of the skin electrodes exceeds a preset level.

* * * * *